United States Patent [19]
Yoshida et al.

[11] 4,061,540
[45] Dec. 6, 1977

[54] CHOLESTEROL OXIDAZE AND PROCESS FOR PREPARING SAME

[75] Inventors: Fumihiko Yoshida, Matsudo; Kiyoshi Mizusawa; Kazuo Nakamura, both of Noda, all of Japan

[73] Assignee: Kikkoman Shoyu Co., Ltd., Noda, Japan

[21] Appl. No.: 700,859

[22] Filed: June 29, 1976

[30] Foreign Application Priority Data

July 4, 1975 Japan .................................. 50-81935

[51] Int. Cl.² ............................................. C12D 13/10
[52] U.S. Cl. ........................................ 195/62; 195/65; 195/66 R
[58] Field of Search ........................ 195/65, 66 R, 62

[56] References Cited

U.S. PATENT DOCUMENTS

| 3,907,642 | 9/1975 | Richmond | 195/66 R X |
| 3,909,359 | 9/1975 | Goodhue et al. | 195/66 R |
| 4,003,794 | 1/1977 | Sugiura et al. | 195/66 R |
| 4,008,127 | 2/1977 | Gruber et al. | 195/65 |

Primary Examiner—Lionel M. Shapiro
Attorney, Agent, or Firm—Schuyler, Birch, Swindler, McKie & Beckett

[57] ABSTRACT

A novel cholesterol oxidase can be obtained by culturing a strain belonging to the Genus Corynebacterium and having an ability to produce cholesterol oxidase in a medium containing cholesterol.

10 Claims, No Drawings

CHOLESTEROL OXIDAZE AND PROCESS FOR PREPARING SAME

This invention relates to a process for preparing cholesterol oxidase with a high efficiency by the use of a strain which belongs to the Genus Corynebacterium and is capable of producing cholesterol oxidase. The invention further relates to providing a cholesterol oxidase which is produced by a microorganism belonging to the Genus Corynebacterium.

More particularly, this invention relates to a process which comprises culturing a novel bacterial species *Corynebacterium cholesterolicum* and preparing cholesterol oxidase from the cultured medium, as well as to a cholesterol oxidase which is prepared by the use of a strain *Corynebacterium cholesterolicum*.

In recent years, the quantitative analysis of cholesterol by the use of cholesterol oxidase is watched with a great interest as a new analytical procedure capable of replacing the hitherto used chemical analysis.

There are known a number of microorganisms capable of producing cholesterol oxidase which include those belonging to, for example, Genus Mycobacterium [Journal of Biological Chemistry, Vol. 206, p. 511 (1954)], Genus Nocardia [Japanese Patent Application Kokai (Laid-Open) No. 44480/1973], Genus Proactinomyces [Japanese Patent Application Kokai (Laid-Open) No. 47582/1974 and the like], as well as Basidiomycetes including Suehirotake [Abstracts for the annual meeting of Nippon Yakugaku-kai (The Pharmaceutical Society of Japan) held in 1975, p. 107].

Most of the microorganisms known to have an ability to produce cholesterol oxidase, however, are disadvantageous in that they are insufficient in the power to produce cholesterol oxidase and that they can produce cholesterol oxidase only in their bacterial cell (the so-called intracellular production of enzymes) so that isolation of the produced enzyme from them necessitates to collect the cultured bacterial cells and then subject them to mechanical rupture, autolysis extraction, etc. which greatly complicates the purification of enzyme and reduces its yield.

A process of producing cholesterol oxidase in the continuous phase of the culture liquid, if it is possible, is expected to be of great practical value in the readiness to recover the enzyme. Heretofore, however, there have hardly been known such type of microorganisms with only one exception of a certain species belonging to Genus Brevibacterium [Japanese Patent Application Kokai (Laid-Open) No. 6773/1975].

In view of above, the present inventors searched for a bacterial strain capable of producing cholesterol oxidase outside the bacterial cell with high stability and high yield extensively in the microbial world. As the result, they discovered a new strain belonging to the Genus Corynebacterium which can produce cholesterol oxidase and found that when this new strain is cultured in a medium in the presence of cholesterol the multiplication of bacterial cell, the inductive production of the enzyme and the accumulation of the enzyme in the continuous phase of culture liquid can be realized simultaneously and therefore said cholesterol oxidase can be prepared in a high yield by on-step procedure not including the conventional extraction from cultured bacterial cells. It was also found that the above-mentioned cholesterol oxidase obtained according to the process of this invention is a novel type of cholesterol oxidase in view of its enzymatic properties mentioned later.

It is an object of this invention to provide a process for preparing cholesterol oxidase which is characterized by culturing in a medium a microorganism belonging to the Genus Corynebacterium and having an ability to produce cholesterol oxidase in the presence of cholesterol and collecting the produced cholesterol oxidase from the cultured medium.

It is another object of this invention to provide a novel cholesterol oxidase.

Other objects and advantages of this invention will become apparent from a further reading of the following description.

The microorganisms used in this invention may by any of the bacterial strains so far as they belong to the Genus Corynebacterium and have an ability to produce cholesterol oxidase. Varieties and mutants thereof may also be used. Concrete example of said strain belonging to the Genus Corynebacterium includes *Corynebacterium cholesterolicum* (ATCC No. 31216, FERM-P No. 3132).

*Corynebacterium cholesterolicum*, referred to above, is a strain which have newly been discovered in a compost containing cattle dung by the inventors, and its bacteriological properties are as mentioned below. The description of bacteriological properties is made in accordance with the manner of "Manual of Microbiological Methods" (published in 1957 by McGraw-Hill Book Company, Inc.).

a. Morphology
Microscopic observation (cultured in a bouillon-agar medium at 30° C for 48 hours)

1. Shape and size of cell:
    i. After a long-term (24–48 hours) cultivation, sphere (0.8–1.0 micron), ovoidfigure or ellipse (0.7–1.0 × 1.1–1.7 micron).
    ii. After a short period of cultivation (3–12 hours), irregular rods (0.7–1.0 × 2.3–9.8 micron) which vary considerably in size and shape and include straight, bent and curved, wedge-shaped, club-shaped, and branching forms.
2. Motility: Not observed.
3. Gram-strain: Positive.
4. Acid-fast: Negative.
5. Spore: Not formed.

b. The state of growth in various media:

1. Bouillon-agar plate culture: Colonies are circular and smooth, convex, translucent and entire, emitting a dim glistening and assuming a pale orange color; 4 mm in diameter after cultured for 48 hours at 30° C.
2. Bouillon-agar slant culture: Growth well, filiform in shape and butyrous in quality, assuming a pale orange color.
3. Bouillon submerged culture: Growth moderate, with membranous pellicle, slight turbidity and powdery sediment.
4. Bouillon-agar stab culture: Growth in the upper layer and stab holes (chain-like).
5. Bouillon-gelatine stab culture: Growth on the surface. No liquefaction.
6. Litmus milk: Formation of membranous pellicle assuming an organelike color. Discoloration of litmus.

No liquefaction and coagulation. Slightly alkaline pH.
7. Potato slant culture: Growth well, pale orange color 2 days after at 30° C, blackening of the potato.

c. Physilogical properties

1. Reduction of nitrates: Positive.
2. Denitrification reaction: Negative.
3. MR test: Negative.
4. VP test: Negative.
5. Formation of indole: Negative.
6. Formation of hydrogen sulfide: Positive.
7. Hydrolysis of starch: Negative.
8. Utilization of citric acid: Negative.
9. Utilization of inorganic nitrogen sources: nitrates, ammonium salts and urea are utilized.
10. Formation of pigment: Not observed (water-soluble pigments).
11. Urease: Positive.
12. Oxidase: Negative.
13. Catalase: Positive.
14. Growth pH: 5–10 (optimum pH 7–8).
15. Growth temperature: 10°–42° C (optimum temperature 30° C).
16. Behavior to oxygen: Aerobic.
17. O-F test: Negative.
18. Formation of acids and gases from sugars: Negative.

|  | Formation of acids | Formation of gases |
|---|---|---|
| 1. Arabinose | — | — |
| 2. Xylose | — | — |
| 3. Glucose | — | — |
| 4. Mannose | — | — |
| 5. Fructose | — | — |
| 6. Galactose | — | — |
| 7. Maltose | — | — |
| 8. Sucrose | — | — |
| 9. lactose | — | — |
| 10. Trehalose | — | — |
| 11. Sorbitol | — | — |
| 12. Mannitol | — | — |
| 13. Inositol | — | — |
| 14. Glycerol | — | — |
| 15. Starch | — | — |

19. Utilization of carbon sources: Glucose, mannose, maltose, trehalose, glycerol and cholesterol are utilized. None of arabinose, xylose, fructose, galactose, sucrose, lactose, sorbitol, mannitol, inositol, dextrin, starch and cellulose is utilized.
20. Liquefaction of gelatine: Negative.
21. Hydrolysis of casein: Negative.
22. Reduction of dyestuffs: Methylene Blue, 2,6-dichlorophenol-indophenol and litmus are reduced.
23. Formation of ammonia: Negative.

By comparing the above-mentioned systematic bacteriological properties of the strain having an ability to produce cholesterol oxidase with the classification mentioned in "Bergey[s Mannual of Determinative Bacteriology, 8th Ed. (1974)", a judgement can be made that the said strain belongs to the Genus Corynebacterium. Respecting species, however, it is found that the said strain does not correspond to any of the known bacterial species. Thus, the said strain can be considered to belong to a new bacterial species.

The reason supporting the above-mentioned judgement is as follows.

The strain used in this invention, having an ability to produce cholesterol oxidase, (ATCC 31216, FERM-P No. 3132) varies its cellular shape from one stage of growth to another. It is a gram-positive, aerobic, non-sporogenous bacterium having no flagella nor motility. Therefore, it is considered to belong to the Genus Corynebacterium. It is regarded as analogous to Corynebacterium eqvi in that its morphological change is close to that of the latter, that it assumes a pale orange color in bouillon-agar plate culture, that it forms a membranous pellicle in bouillon submerged culture and that it reduces nitrates to yield nitrous acid. As shown in Table 1, however, it belongs to a new bacterial species different from Corynebacterium eqvi in that it differs from the latter in some properties.

Table 1

| Item | Corynebacterium eqvi | Bacterium of this invention |
|---|---|---|
| Litmus milk | No change | Reduction of the litmus |
| Urease | − | + |
| Fermentation of glucose | + | − |
| Utilization of glucose | Slow | Rapid |
| Utilization of chlolesterol | − | + |
| Resistance to 2.5% oxalic acid | + | − |

For the reasons mentioned above, this bacterium is regarded as a new strain and is named Corynebacterium cholesterolicum.

The strain used in this invention is deposited in Fermentation Research Institute, Agency of Industrial Science and Technology, Chiba, Japan as FERM-P No. 3132 and in American Type Culture Collection as ATCC 31216.

The method of preparing cholesterol oxidase by use of this strain is mentioned below.

It is usually preferably to employ liquid culture. Industrially, it is advantageous to employ aeration-agitation submerged culture. In the medium used in this invention, the nitrogen source may be any of the utilizable nitrogen compounds, among which urea is most preferable. Other usable nitrogen sources include nitrates such as sodium or potassium nitrate, ammonium salts such as ammonium sulfate, ammonium chloride, ammonium phosphate etc. and organic nitrogen sources such as amino acids, peptone, meat extract, yeast extract, corn steep liquor and the like. The medium contains at least one kind of the above-mentioned nitrogen source with which may be incorporated, appropriately, at least one kind of inorganic salt. Concrete examples of said inorganic salt include potassium phosphate, magnesium sulfate, calcium carbonate, potassium chloride and the like. If necessary, other substances necessary for the growth of bacteria or the production of enzyme, such as sugar materials, various organic and inorganic compounds, vitamins and the like, may be further added to the medium.

In this invention, the above-mentioned strain is cultured in the presence of cholesterol. Thus, it is permitted to culture the strain in a medium preliminarily prepared by incorporating cholesterol into the above-mentioned culture medium. Otherwise, it is also permitted to culture the strain by adding cholesterol to the medium within 48 hours after the start of cultivation.

The amount of cholesterol to be added is in the range of 0.5 to 10% (W/V), preferably 1 to 3% (W/V), based on the total volume of medium.

The strain capable of producing cholesterol oxidase is inoculated into and cultured in a medium which has been prepared by appropriately combining the above-mentioned carbon course, nitrogen source, inorganic compound and organic compound to give a fundamental culture medium composed of, for example, cholesterol, urea, potassium primary phosphate, potassium secondary phosphate, magnesium sulfate, potassium chloride and yeast extract, adjusting pH value of the medium to 7.0–8.0, and sterilizing it at an elevated temperature in the usual manner.

Although the culture temperature may be varied in the range permitting the growth of cholesterol oxidase producing bacteria and the production of cholesterol oxidase, the temperature is preferably in the range of 25° to 35° C.

Although the time period of culture varies with its form, an effective production and accumulation of cholesterol oxidase in the culture liquid can be accomplished within 72 hours by inoculating the cholesterol oxidase producing strain into the medium and culturing it in an aerobic condition by means of shaking culture or aeration-agitation culture.

The method for collecting cholesterol oxidase from the cultured product after completion of the culture of this invention is mentioned below.

First of all, Triton X-100 (Tradename for polyoxyethylene alkylphenol ether manufactured by Rohm and Haas Co.) is added to the culture liquid in an amount of 0.1–1.0% (V/V) and the resulting mixture is stirred for 1 hour at a temperature below the room temperature, after which a cationic surfactant, such as benzethonium chloride or benzalkonium chloride, is added in an amount of 0.01–0.1% (W/V) and the resulting mixture is homogenized and allowed to stand for more than 1 hour. By this treatment, the bacterial cells present in the culture liquid are readily coagulated and precipitated. Subsequently, the culture liquid is filtered by the use of celite such as Hyflo Super-Cell (manufactured by Johns-Manville Sales Co.) or is centrifuged, whereby a perfectly limpid enzyme solution is obtained. Subsequently, the limpid solution is concentrated to one-fifth to one-tenth of its original volume by means of conventional concentrating procedure such as concentration uder reduced pressure, ultrafiltration or the like.

Powdery specimen of the crude enzyme can be obtained from the concentrated solution by means of the conventional method of recovering enzyme such as salting out with ammonium sulfate, precipitation with organic solvent or the like. However, it is also obtainable by simple procedure which comprises dialyzing the concentrated solution against water or a dilute buffer solution by use of an ultrafilter and then freeze-drying the dialyzed solution.

The considered strain produces cholesterol oxidase not only in the continuous phase of culture liquid but also inside the bacterial cells. The enzyme produced in the bacterial cells can be recovered in the form of crude enzyme in the following manner. First of all, the bacterial cells are separated from the culture liquid by an appropriate procedure. Subsequently, the bacterial cells are destructed by a disclosed procedure such as grinding with a grinding material, enzymatic bacteriolysis with lysozyme etc., application of supersonic energy, or application of osmotic shock. Otherwise, the bacterial cells are shaken or allowed to stand in the presence of toluene or the like until they have been self-digested, whereby the enzyme is liberated out of the bacterial bodies. Subsequently, the solid material is removed from the resulting mixture by an appropriate procedure such as filtration, centrifugation or the like. Finally, the bacterial extract thus obtained is treated in accordance with the afore-mentioned method for recovering enzyme.

The enzymatic properties of the cholesterol oxidase obtained according to the process of this invention are as mentioned below:

1. The action and substrate specificity

This enzyme oxidizes the hydroxyl group of steroids at 3$\beta$ position, and exerts no action upon other position of hydroxyl groups, such as 3$\alpha$, 17$\beta$, etc., nor upon ester groups. As seen in Table 2, it entirely differs from the analogous enzymes hitherto known in having an outstandingly strong activity to pregnenolone which has been measured by the method as hereinafter described among the many 3$\beta$-hydroxysteroids. In fact, the relative activities of various enzymes exhibited to pregnenolone and cholesterol are as follows: this enzyme 4.16, the enzyme of *Nocardia erythropolis* 0.82, and the enzyme of *Brevibacterium sterolicum* 0.22.

The crude enzyme specimen obtained as above can be purified to give pure cholesterol oxidase by combining several means of purification, such as ion-exchange chromatography by use of CM-Sephadex, DEAE-Sephadex or the like, gel filtration by use of Sephadex G-100, etc., and practicing the combined means under appropriate conditions.

Table 2

| Action and Substrate-specificity | |
| --- | --- |
| Substrate | Relative activity (%) |
| Cholesterol | 100 |
| Dehydro-epiandrosterone | 57 |
| Pregnenolone | 416 |
| $\beta$-Sitosterol | 54 |
| $\beta$-Cholestanol | 43 |
| Stigmasterol | 17 |
| Ergosterol | 13 |
| Digitoxigenin | 0 |
| Diosgenin | 0 |
| $\beta$-Estradiol | 0 |
| Vitamin $D_3$ | 0 |
| Cholic acid | 0 |
| Androsterone | 0 |
| Testosterone | 0 |
| Cholesterol acetate | 0 |

All the above-mentioned values of relative activity (%) refer to the relative amounts of hydrogen peroxide formed from the substances oxidized by cholesterol oxidase, where the activity to cholesterol is taken as 100. The activity was measured by the following procedure.

A substrate solution was prepared by mixing 50 microliter of a 0.38 micromolar solution of cholesterol in isopropanol with 3 milliliter of 0.1 M phosphate buffer (pH 7.0; it contains 0.82 millimoles of 4-aminoantipyrine, 14 millimoles of phenol, 0.17 millimoles of Carbowax 6000 and 0.3% Triton X-100). The resulting substrate solution was incubated for 5 minutes in a cell of light path, 10 mm, kept at 37° C.

50 microliter of an enzyme solution containing 2.5 U of peroxidase and 0.1 U of cholesterol oxidase was added. The increase in absorbance at 500 nm was measured at 37° C. The initial velocity was obtained from the increase in absorbance, from which the relative activity was computed. [Literature: Charles C. Allain, Lucy S. Poon, Cicely G. Chan, W. Richmond and Paul C. Fu, Clin. Chem. 20, 470 (1974)].

The above-mentioned characteristic properties of the present enzyme are quite favorable when one wishes to synthesize progesterone a corpus luteum hormone from prognenolone enzymatically.

As is well known, progesterone is an important substance as a "key metabolite" for the biosynthesis of various steroid hormones and, in addition, has variegated physiological activities in itself. Practically, it is used as a corpus luterum hormone preparation frequently in the fields of obstetrics and gynecology.

In converting prognenolone into progesterone, the use of this enzyme is far more advantageous to the use of other enzymes. Therefore, the enzyme of this invention is far more hopeful in the practical effect than the hitherto disclosed cholesterol oxidases.

2. Optimum pH

The optimum pH is in the vicinity of 7.0 when the substrate is cholesterol.

3. Stability

It keeps stable in the pH range of 5–9 when treated at 30° C for 1 hour. A heat stability test (a treatment for 30 minutes) has revealed that it is entirely stable at 50° C whereas 94% of its activity is lost at 60° C.

4. Optimum temperature for the action

When the reaction time is 15 minutes, the optimum temperature is 40° C.

5. $K_m$ value $K_m$ for cholesterol and prognenolone, as measured by the ultraviolet absorption method, are $5.4 \times 10^{-5}$ M and $3.1 \times 10^{-5}$ M, respectively.

6. Inhibition

This enzyme is inhibited by p-chloromercuribenzoate and heavy metal ions, such as $Hg^{2+}$ and $Ag^+$, whereas it is not inhibited by metal chelates or chelate-forming reagents such as EDTA, o-phenanthroline, 8-hydroxyquinoline, KCN and the like.

7. Homogeneity

Homogeneity of the purified enzyme has been confirmed by the disk electrophoresis method. Thus, an electrophoresis was carried out according to the method of Davis [Ann. N.Y. Acad. Sci., 121, 404 (1964)] with a constant electric current of 3 mA per one column by the use of a standard gel (5 × 65 mm) and 50 millimolar acetate-$\beta$-alanine buffer (pH 4.5). After the electrophoresis, the sample was dyed with 1% Amido Black and the excessive dyestuff was removed by passing a constant electric current of 8 mA per one column. As the result, the purified enzyme showed a single band.

8. Molecular weight

It has a molecular weight of 57,000 as measured by the SDS disk electrophoresis method. Thus, an electrophoresis was carried out according to the method of Weber [J. Biol. Chem., 244, 4406 (1969)] with a constant electric current of 8 mA per one column by the use of 10% gel (5 × 75 mm) and 0.1% SDS-0.1 M phosphate buffer (pH 7.2). After the electrophoresis, the sample was dyed with Coomassie Brilliant Blue R-250. The decolorization was carried out in a stirred 10% acetic acid. The molecular weight was determined by reference to the mobility of a standard protein (trypsin, pepsin, ovoalbumin and cattle serum albumin). Speaking for reference, the analogous cholesterol oxidases hitherto disclosed have the following molecular weights: 32,500 for *Brevibacterium sterolicum*. [Literature: T. Uwajima, H. Yagi and O. Terada, Agr, Biol. Chem. 38, 1149 (1974)].

9. Crystal structure

None has ever succeeded in crystallizing this enzyme.

10. Isoelectric point

The enzyme has an isoelectric point of pH 8.7, as measured by the method of isoelectric focusing. Thus, 10 mg of a purified enzyme was introduced into a 110 ml column packed with a carried ampholyte kept at pH 3-10 [LKB-Producter, commercial name of a product manufactured by AB Co.; cf. Biochem. Biophys. Acta, 133, 435 (1967)]. An electric current was passed at a voltage of 900 V for a period of 50 hours, while the column was cooled to 4° C. As the result, a peak of single protein, having an enzymatic activity, was observed at pH 8.7.

11. Absorption spectrum

The purified enzyme shows absorption maxima at 280 nm which is assignable to the protein, as well as at 390 nm and 470 nm.

12. Coenzyme

The absorption spectrum suggests that this enzyme contains FAD as a coenzyme.

Method for Measuring the Enzymatic Activity

Enzymatic activity was measured by ultraviolet absorption method [Clin. Chem. 20, 470 (1974)]. A substrate solution was prepared by dissolving 5 ml of a 300 mg/dl solution of cholesterol in isopropanol into 300 ml of phosphate buffer (pH 7.0) containing 0.05% of Triton X-100. 20 microliter of enzyme solution was added to 3.0 ml of the substrate solution, and the resulting mixture was reacted at 37° C for 15 minutes. Increase in the absorption at 240 nm, assignable to cholest-4-en-3-one resulting from the reaction, was measured.

The Unit of Enzymatic Activity

One unit of cholesterol oxidase was defined as the quantity of enzyme with which one micromole of cholesterol is decomposed in one minute. Specific activity was represented by the enzymatic unit number per 1 milli-gram protein.

Quantitative Analysis of Protein

The concentration of protein was determined by the method of Lowry et al. [J. Biol. Chem., 193, 265 (1951)] with human serum albumin as a standard protein.

It is concluded that the cholesterol oxidase obtained by the method of this invention is a novel enzyme in view of the facts that it is far higher in the activity to prognenolone than the analogous enzymes hitherto known and that it has a very high molecular weight [preceding paragraphs (1) and (8)].

The following examples will further concretely illustrate this invention but are not to be considered limitations thereupon.

EXAMPLE 1

50 ml portions of a culture medium containing 3% cholesterol, 0.9% urea, 0.1% yeast extract, 0.1% $KH_2PO_4$, 0.3% $K_2HPO_4$, 0.05% $MgSO_4 \cdot 7H_2O$ and 0.1% KCl and having a pH value of 7.2, were separately placed in shaking flasks of 500 ml capacity. They were sterilized at an elevated temperature of 120° C for 5 minutes. Subsequently, they were inoculated with one platinum loop quantity of *Corynebacterium cholesterolicum* (ATCC 31216, FERM-P No. 3132), taken out from an agar slant culture, and subjected to a shaking culture at 30° C for 72 hours with an amplitude of 7 cm at a speed of 140 s.p.m.

After completion of the culture, the resulting culture liquid was centrifuged and the supernatant was taken out, which was a crude enzyme solution. The latter had a cholesterol oxidase activity of 2.35 units/ml.

EXAMPLE 2

To a medium having the same composition as referred to in Example 1 was added Tween 80 in a quantity of 0.01% by weight based on the total volume of the medium, after which the medium was treated in the same manner as in Example 1. Into the heat-sterilized medium thus obtained was inoculated one platinum loop quantity of *Corynebacterium cholesterolicum* (ATCC 31216, FERM-P No. 3132), taken out from an agar slant culture, and it was subjected to shaking culture at 30° C for 72 hours with an amplitude of 7 cm at a speed of 140 s.p.m.

After completion of the culture, the culture liquid was centrifuged and the supernatant was taken out, which was a crude solution. The latter had a cholesterol oxidsae activity of 2.6 units/ml.

EXAMPLE 3

50 ml portions of a culture medium containing 1% cholesterol, 0.2% $(NH_4)_2SO_4$, 0.1% yeast extract, 0.5% $CaCO_3$, 0.1% $KH_2PO_4$, 0.3% $K_2HOP_4$, 0.1% KCl, 0.05% $MgSO_4 \cdot 7H_2O$ and 0.01% Tween 80 and having a pH value of 7.2, were separately placed in shaking flasks of 500 ml capacity. After being sterilized at an elevated temperature of 120° C for 15 minutes, they were inoculated with one platinum loop quantity of *Corynebacterium cholesterolicum* (ATCC 31216, FERM-P No. 3132), taken out from an agar slant culture, and subjected to shaking culture at 30° C for 72 hours with an amplitude of 7 cm at a speed of 140 s.p.m.

After completion of the culture, the culture liquid was centrifuged and the supernatant was separated, which was a crude enzyme solution. The latter had a cholesterol oxidase activity of 0.5 unit/ml.

EXAMPLE 4

To a culture medium having the same composition as mentioned in Example 1 was added Tween 80 in an amount of 0.01% by weight based on the total volume of the medium. 20 liters of the modified medium thus obtained was placed in a jar fermenter of 30 liter capacity and sterilized at 120° C instantaneously. After being cooled, it was inoculated with 1% quantity of a culture liquid containing *Corynebacterium cholesterolicum* (ATCC 31216, FERM-P No. 3132) which had been cultured in the same medium as above at 30° C for 48 hours in a shaking flask. Subsequently, it was cultured at 30° C for 72 hours at aerating speed of 15 liters/min. and a rotating speed of 300 r.p.m.

After completion of the culture, the supernatant layer of the culture liquid was separated, which was a crude enzyme solution. The latter had a cholesterol activity of 4.0 units/ml. 10 liters of the fermented solution thus obtained was centrifuged to remove the remaining bacterial bodies and other solid materials. The transparent supernatant thus obtained was concentrated to one-tenth of the original volume by means of ultrafiltration. The concentrate was cooled to a temperature below 5° C, into which was slowly added and dissolved pulverized ammonium sulfate with stirring until the concentration of ammonium sulfate reached a value of 75% saturation. The mixture was allowed to stand overnight, after which the resulting coagulates were separated and recovered. The solid material thus obtained was dissolved into 0.01 M phosphate buffer (pH 7.0) and completely dialyzed against the same buffer kept at 4° C. The dialyzed solution, after being freeze-dried, gave 60 g of crude enzyme powder having an activity of 500 units/g. The recovery rate was 75%.

EXAMPLE 5

The bacterial cell fraction isolated from the fermented solution obtained in Example 4 was suspended into a five times greater volume of 0.01 M phosphate buffer (pH 7.0). A small quantity of toluene was added and the resulting mixture was allowed to stand at 37° C for 2 hours. Subsequently, it was centrifuged to remove the solid material. The bacterial cell extract solution thus obtained was treated by the same procedure as in Example 4 to give 11 g of a crude enzyme powder having an activity of 600 units. The recovery rate was 65%.

EXAMPLE 6

The present example is concerned with the purification of the cholesterol oxidase obtained by the process of this invention.

Step 1: Preparation of Limpid Broth 20 liters of a medium (pH 7.2) containing 1.5% cholesterol, 0.6% urea, 0.1% yeast extract, 0.1% $KH_2PO_4$, 0.3% $K_2HPO_4$, 0.05% $MgSO_4 \cdot 7H_2O$ and 0.1% KCl was placed in a jar fermenter of 30 liter capacity, instantaneously sterilized at 120° C, and cooled. On the other hand, 50 ml of a medium having the same composition as above was placed in a shaking flask of 500 ml capacity, instantaneously sterilized at 120° C, cooled, inoculated with one platinum loop quantity of *Corynebacterium cholesterolicum* (ATCC 31216, FERM-P No. 3132) taken out from an agar slant culture, and subjected to a shaking culture at 30° C for 24 hours. The resulting culture liquid was inoculated into the first medium in an amount of 2% and cultured at 30° C for 48 hours at an aerating speed of 15 liters/min. and a rotating speed of 260 r.p.m.

After completion of the culture, polyoxyethylene alkylphenol ether (Triton X-100, nonionic surfactant manufactured by Rhom and Haas Co.) was added in an amount of 0.4% and the resulting mixture was stirred at room temperature for 1 hour. Subsequently, a 10% solution of benzethonium chloride (Hiamine Liquor, a cationic surfactant manufactured by Sankyo K.K.) was added in an amount of 0.6% (V/V). The resulting mixture was allowed to stand for 1 hour and then filtered by use of Hyflo Super-Cell.

Step 2: Concentration and Dialysis

The limpid solution thus obtained was concentrated to one-fifth of the original volume by means of a flash evaporator. The concentrate (500 ml) was dialyzed against a five times greater volume of 0.01 M phosphate buffer (pH 7.0) containing 0.01% Triton X-100 by use of an ultrafilter (Diaflow Membrane PM 30, type TCF 10, manufactured by Amicon Co.) and then concentrated to one half of the original volume. The precipitate, formed after the dialysis, was removed by filtration.

Step 3: Chromatography on CM-Sephadex Column 125 ml of the dialyzed solution was introduced into a column (2.5 × 50 cm) packed with CM-Sephadex which had preliminarily been buffered with 0.01 M phosphate buffer (pH 7.0) containing 0.5% Triton X-100. The column had preliminarily been washed with the same buffer as above to remove protein contaminates containing a large quantity of yellow pigment. After introduction of the dialyzed solution, the enzyme was eluted out with 0.1 M phosphate buffer containing 0.5% Triton X-100. The above-mentioned procedure was repeated twice to treat 250 ml of the dialyzed solution. The active fraction was concentrated to 100 ml by means of an ultrafilter and again dialyzed against a five times greater volume of 0.01 M carbonate buffer (pH 9.2).

Step 4: Chromagography on DEAE-Sephadex 100 ml of the dialyzed solution was adsorbed to a DEAE-Sephadex column (2.5 × 50 cm) preliminarily buffered with 0.01 M carbonate (pH 9.2). The elution was started with 0.01 M carbonate buffer (pH 9.2), and then a linear gradient elution was carried out with 0.01 M carbonate buffer (pH 9.2) containing 0.08 M of sodium chloride so that the final concentration was 0.08 M sodium chloride, whereby the enzyme was eluted out. The active fraction was concentrated to 10 ml and dialyzed against 0.01 M phosphate buffer (pH 8.0) containing 0.1 M sodium chloride.

Step 5: Gel Filtration by Use of Sephadex G-100

10 ml of the dialyzed solution was gel-filtered with Sephadex G-100. Sephadex G-100 had been packed into a 2.5 × 100 cm column and preliminarily washed with 0.01 M phosphate buffer (pH 8.0) containing 0.1 M sodium chloride. A protein was eluted out, of which peak formed a symmetrical shape. The rise and fall of enzymatic activity just coincided with the protein peak. The enzyme fraction had a volume of 70 ml. After being concentrated, it assumed yellow.

Results of the purification are summarized in Table 3.

Table 3

Summarized Results of the Purification

| Fraction | Volume (ml) | Protein (mg) | Specific activity (u/mg) | Yield (%) |
|---|---|---|---|---|
| Step: | | | | |
| 1. Supernatant of broth | 2,500 | 5,500 | 0.51 | 100 |
| 2. Concentration and dialysis | 250 | 3,040 | 0.84 | 91 |
| 3. CM-Sephadex | 100 | — | — | 67 |
| 4. DEAE-Sephadex | 10 | 51 | 6.5 | 11 |
| 5. Sephadex G-100 | 70 | 26 | 8.4 | 7.8 |

What is claimed is:

1. Cholesterol oxidase which is produced by a microorganism belonging to the species *Corynebacterium cholesterolicum*, has a molecular weight of 57,000 as measured by Weber's SDS disk electrophoresis, and oxidizes the hydroxyl group attached to the 3β-position of steroids and exerts no action upon the hydroxyl groups attached to other positions nor upon esters.

2. A process for preparing cholesterol oxidase which comprises culturing, in a medium in the presence of cholesterol, a microorganism belonging to the species *Corynebacterium cholesterolicum* and having an ability to produce cholesterol oxidase and collecting the cholesterol oxidase from the cultured medium.

3. A process according to claim 2, wherein the microorganism belonging to the Genus Corynebacterium is *Corynebacterium cholesterolicum* (FERM-P No. 3132, 4. A process according to claim 2, wherein cholesterol is added into the medium within 48 hours after the start of culture.

5. A process according to claim 2, wherein said medium contains at least one member selected from the group consisting of urea, nitrates, ammonium salts, amino acids, peptone, meat extract, yeast extract and corn steep liquor as a nitrogen source and at least one member selected from the group consisting of potassium phosphate, potassium chloride, magnesium sulfate and calcium carbonate as an inorganic salt.

6. A process according to claim 2, wherein the amount of cholesterol in said medium is in the range of 0.5 to 10% (W/V) based on the total volume of the medium.

7. A process according to claim 2, wherein the culture is effected at 25° to 35° C, for within 72 hours at pH 7.0–8.0.

8. A process according to claim 2, wherein the cultured medium is treated with Triton X-100 and then Hiamine Liquor.

9. Cholesterol oxidase according to claim 1, wherein the microorganism belonging to the species *Corynebacterium cholesterolicum* is *Corynebacterium cholesterolicum* (FERM-P No. 3132, ATCC 31216.)

10. A process according to claim 2, wherein the cultured medium is the culture liquid and bacterial cells or the culture liquid.

* * * * *